United States Patent
Brown et al.

(10) Patent No.: US 11,426,476 B2
(45) Date of Patent: Aug. 30, 2022

(54) INTERNAL ULTRAVIOLET LED ANTIFOULING

(71) Applicant: The United States of America as Represented by the Secretary of the Navy, San Diego, CA (US)

(72) Inventors: Michael Hunter Brown, La Jolla, CA (US); Nicholas Ray Caruso, San Diego, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 344 days.

(21) Appl. No.: 16/712,588

(22) Filed: Dec. 12, 2019

(65) Prior Publication Data

US 2021/0177998 A1   Jun. 17, 2021

(51) Int. Cl.
| | |
|---|---|
| *A61L 2/10* | (2006.01) |
| *B63B 59/04* | (2006.01) |
| *B63B 59/08* | (2006.01) |
| *C02F 1/32* | (2006.01) |
| *B08B 17/02* | (2006.01) |

(52) U.S. Cl.
CPC ............... *A61L 2/10* (2013.01); *B08B 17/02* (2013.01); *B63B 59/04* (2013.01); *B63B 59/08* (2013.01); *C02F 1/325* (2013.01); *C02F 2201/3222* (2013.01)

(58) Field of Classification Search
CPC ........ A61L 2/10; A61L 2202/11; B08B 17/02; B63B 59/04; B63B 59/08; C02F 1/325; C02F 2201/3222
See application file for complete search history.

(56) References Cited

U.S. PATENT DOCUMENTS

| | | | |
|---|---|---|---|
| 5,322,569 A | 6/1994 | Titus | |
| 6,311,546 B1 | 11/2001 | Dickinson | |
| 6,579,495 B1 * | 6/2003 | Maiden .................. | C02F 1/325 210/748.11 |
| 7,276,736 B2 * | 10/2007 | Hohn .................. | C09K 11/7749 313/503 |
| 7,713,558 B2 | 5/2010 | Riquelme Salamanca | |
| 7,862,728 B2 * | 1/2011 | Yencho .................. | C02F 1/325 210/748.01 |
| 8,324,595 B2 * | 12/2012 | Takahashi ............... | C02F 1/325 250/435 |
| 9,562,163 B2 | 2/2017 | Lobe | |
| 10,986,716 B2 * | 4/2021 | Van Delden ........... | H05B 45/37 |
| 11,339,961 B2 * | 5/2022 | Leijssen .................. | A61L 2/26 |

(Continued)

FOREIGN PATENT DOCUMENTS

| | | | | |
|---|---|---|---|---|
| DE | 102014118672 B3 | * | 10/2015 | ....... B29C 45/14639 |
| WO | WO-2016095901 A | * | 6/2016 | ....... B29C 45/14639 |

*Primary Examiner* — Regina M Yoo
(74) *Attorney, Agent, or Firm* — Naval Information Warfare Center, Pacific; Kyle Eppele; James McGee

(57) ABSTRACT

An internal ultraviolet-C light emitting diode antifouling system and method that include a waterproof, light transmissible potted enclosure; an object disposed within the waterproof, light transmissible potted enclosure; and at least one ultraviolet-C light emitting diode disposed within the waterproof, light transmissible enclosure, wherein the at least one ultraviolet-C light emitting diode is configured to emit light on the object, wherein the light is configured to prevent biofouling on the object.

18 Claims, 3 Drawing Sheets

(56) References Cited

U.S. PATENT DOCUMENTS

| | | | |
|---|---|---|---|
| 2006/0189686 A1 | 8/2006 | Martensson | |
| 2011/0127448 A1* | 6/2011 | Ben-Shmuel | C02F 1/008 |
| | | | 250/492.1 |
| 2011/0226966 A1* | 9/2011 | Takahashi | C02F 1/325 |
| | | | 250/492.1 |
| 2014/0083931 A1 | 3/2014 | Chang | |
| 2015/0313354 A1* | 11/2015 | Mongan | A46B 17/06 |
| | | | 15/105 |
| 2016/0068240 A1 | 3/2016 | Swain | |
| 2017/0334114 A1* | 11/2017 | Sticklus | F21V 31/04 |

* cited by examiner

INTERNAL ULTRAVIOLET LED ANTIFOULING

The United States Government has ownership rights in this invention. Licensing inquiries may be directed to Office of Research and Technical Applications, Naval Information Warfare Systems Center, Pacific, Code 3600, San Diego, Calif., 92152; telephone (619)553-3001; email: ssc_pac_t2@navy.mil. Reference Navy Case No. 105,004.

BACKGROUND OF THE INVENTION

Field of the Invention

The present disclosure relates generally to maintenance of underwater objects and, more particularly, to preventing biofoul growth on underwater objects.

Description of Related Art

Keeping marine life from growing on underwater objects, such as sensors or rudders, deployed in the water column is a difficult challenge. This marine life may be referred to as biofouling. Biofouling can prevent successful data acquisition from electronics such as sensors. It is also an irritant for both deployment and recovery.

Older methods of cleaning biofouling involved painting the underwater objects, e.g., cables/arrays, with an antifouling paint, which is expensive and presents health risks. This can be relatively effective for certain scenarios, but the paint may lose its effectiveness after about twelve (12) months of continuous deployment. Further, this paint is a serious health hazard for painting and post paint handling. Finally, this paint is typically cured in ovens, meaning that housings must be masked and painted separately, adding delays to the total project timeline.

There is a need for a biofouling system that does not present the hazards of paint.

SUMMARY OF THE INVENTION

Aspects of the present disclosure provide an internal ultraviolet-C light emitting diode antifouling system, comprising: a waterproof, light transmissible potted enclosure; an object disposed within the waterproof, light transmissible potted enclosure; and at least one ultraviolet-C light emitting diode disposed within the waterproof, light transmissible enclosure, wherein the at least one ultraviolet-C light emitting diode is configured to emit light on the object, wherein the light is configured to prevent biofouling on the object.

BRIEF DESCRIPTION OF THE DRAWINGS

The accompanying drawings, which are incorporated in and form a part of the specification, illustrate example embodiments and, together with the description, serve to explain the principles of the invention. In the drawings.

DETAILED DESCRIPTION

Aspects of the present disclosure provide for preventing biofoul growth on an object, such as an underwater object, which may be, e.g., a sensor in an array node of an array cable. Such biofoul prevention may occur using an ultraviolet-C light emitting diode (LED) that emits blinking light on the underwater object. The object and the ultraviolet-C LED may be enclosed in a substantially waterproof, light-transmissible material such as fused quartz which may, in turn, be disposed in an array node of an array cable. The ultraviolet-C LEDs inside the array nodes of the array cable may blink at a certain rate in order to kill organism growth and stop the fouling process. No harmful chemicals or pollutants are used to prevent fouling, thus making the present system and method safer for the environment. More reliable data may be recorded from underwater objects, such as clean array sensors, with no fouling.

Figure 1:
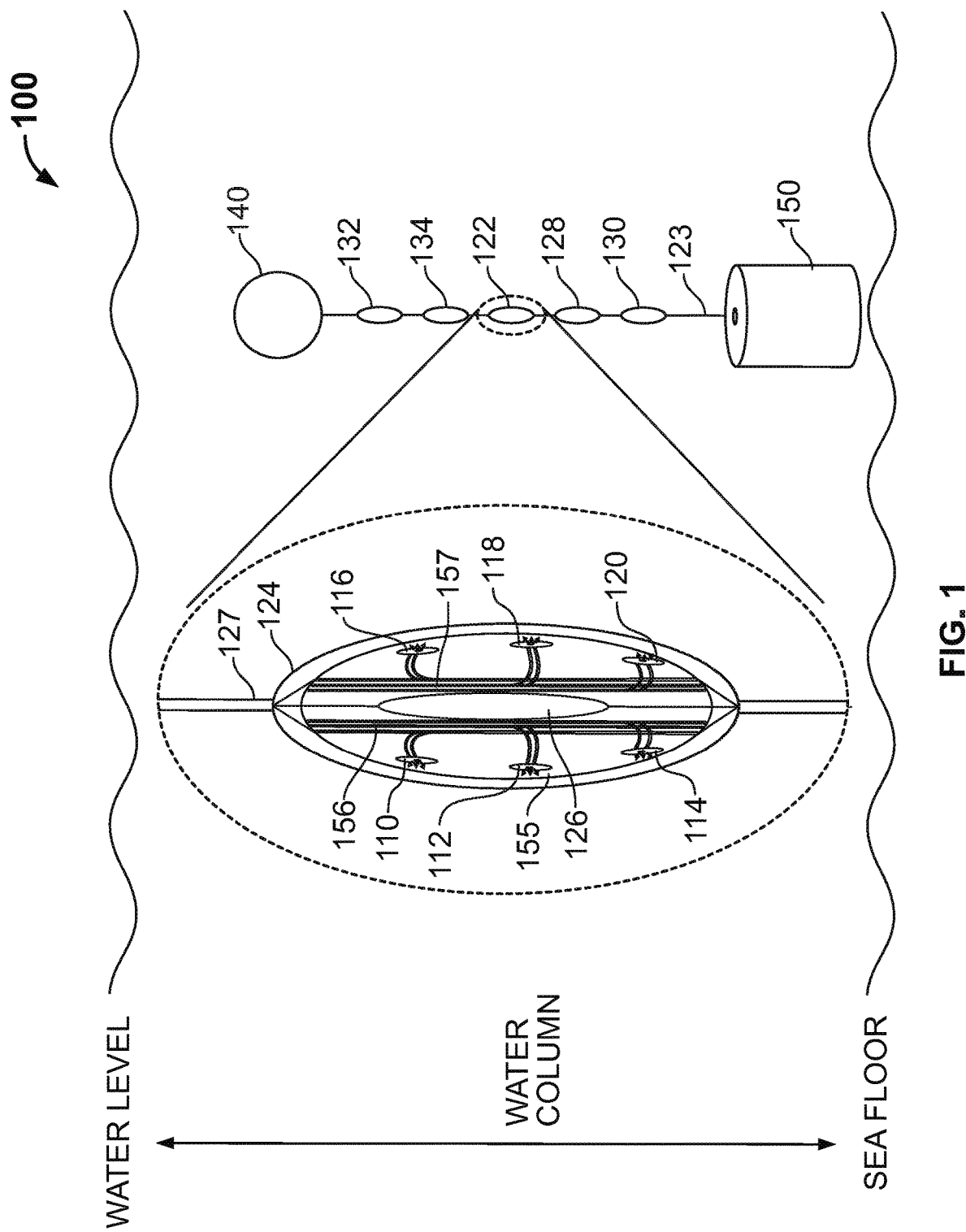
FIG. 1 illustrates a system for internal ultraviolet-C light emitting diode (LED) antifouling in accordance with aspects of the present disclosure.

Referring now to FIG. 1, illustrated is an internal ultraviolet-C LED system in accordance with one embodiment of the present disclosure. The internal ultraviolet-C LED antifouling system 100 includes multiple ultraviolet-C LEDs 110, 112, 114, 116, 118, 120 potted inside array node 122 of an array cable 123. A waterproof, light transmissible potted enclosure 124 encloses the multiple ultraviolet-C LEDs 110, 112, 114, 116, 118, 120 and an underwater object 126, such as a sensor. The multiple ultraviolet-C LEDs may be configured to emit ultraviolet-C light to clean the waterproof, light transmissible potted enclosure 124 so that underwater object 126, which may be an underwater sensor, works properly and records accurate data.

The number of ultraviolet-C LEDs that are needed to clean the waterproof, light transmissible potted enclosure 124 may be location dependent. For example, warmer climates, where more biofouling occurs, may require a greater number of ultraviolet-C LEDs. Also by way of example, the deeper the internal ultraviolet-C LED antifouling system 100 is placed in the water, the more ultraviolet-C LEDs may be needed because more ultraviolet-C light is needed to permeate a murky underwater environment. A person of ordinary skill in the art would be able to determine the number of ultraviolet-C LEDs needed for a particular application.

As is known in the art, ultraviolet light generally falls within three categories: ultraviolet-A, ultraviolet-B and ultraviolet-C light. Ultraviolet-C light is short wavelength ultraviolet light that may break apart biofouling, leaving it unable to function or reproduce. The present system and method may incorporate ultraviolet-C light in the ultraviolet-C LEDs 110, 112, 114, 116, 118, 120 to help prevent biofouling on underwater object 126 such as a sensor. The underwater object 126 may be disposed within the waterproof, light transmissible potted enclosure 124. Wiring 127 for the underwater object may run along the array cable, both inside and outside the waterproof, light-transmissible potted enclosure 124 disposed in array node 122. In addition to array node 122, other array nodes 128, 130, 132, 134 are disposed in array cable 123.

A positioning assembly positions the ultraviolet-C LEDs and includes a fixed buoyancy mechanism such as float 140 and an anchor 150. Float 140 or air bladder keeps the array cable 123 positioned in the substantially vertical water column, which may position the entire ultraviolet-C LED antifouling system 100 in a desired position underwater. The anchor 150, which may be a sensor and battery bottle, anchors the array cable 123 down to the seafloor. Battery length can be extended by flashing the ultraviolet-C LED's at a certain rate known in the art to kill the organism growth that prefaces significant fouling, rather than keeping the light on. The optimal time on and time off lengths required to keep the nodes clean may vary. The anchor 150 is attached to a second end of the array cable 123. The anchor 150 may be a sensor and battery bottle that may be used to contain relevant acoustics processing electronics and storage media for an underwater object 126 such as the illustrated underwater cable/array. In this implementation, in lieu of a sensor and battery bottle, another form of anchor 150 or tethering device would be sufficient to ensure the underwater object 126 is oriented substantially vertically in the water column.

Potting is known in the art, and the potting process may include filling an electronic assembly that is placed in a mold with a potting compound 155. The potting compound 155 may be a solid or gel, such as a thermosetting plastic or a silicone rubber gel. The electronic assembly which may include the object 126, ultraviolet-C LEDs 110, 112, 114, 116, 118, 120 along with ultraviolet-C LED wiring 156, 157 may be placed inside a mold. The potting process may be used to make the potted electronics resistant to impact, tremors and vibrations, and to stop corrosive elements and moisture from entering the electronics. In the present illustration, the waterproof, light transmissible potted enclosure is composed of fused quartz. A material such as fused quartz may allow lower light wavelengths to pass through, and thus allows ultraviolet-C light to pass through. Other suitable materials may include quartz glass and O-rings to waterproof the needed items. In some situations, liquid quartz such as the spray that is commercially available from Made of Australia may be used. On the other hand, other common types of enclosures, such as polycarbonate or acrylic may block the ultraviolet-C light, and may not be suitable for the internal ultraviolet-C LED antifouling system described herein.

The thickness of the waterproof, light transmissible potted enclosure 124 may vary depending on the depth at which the ultraviolet-C LED antifouling system is intended to operate. The ultraviolet-C LED antifouling system 100 needs to be pressure tolerant for the depth of water in which the ultraviolet-C LED antifouling system 100 is expected to operate. The ultraviolet-C LEDs 110, 112, 114, 116, 118, 120 may point outward from the sensor, thus illuminating the waterproof, light transmissible potted enclosure 124 and killing biofouling, including bacteria.

The ultraviolet-C LEDs 110, 112, 114, 116, 118, 120 may be configured to blink at a rate and time that removes biofouling from the underwater object 126. The longer the ultraviolet-C LEDs 110, 112, 114, 116, 118, 120 blink, the more likely biofouling is to be removed. It may be desirable to keep the lights blinking as long as possible, but also to conserve power needed for the ultraviolet-C LED antifouling system 100. Therefore, a duty cycle of fifty percent (50%) on and 50% off may be desirable.

Figure 2:
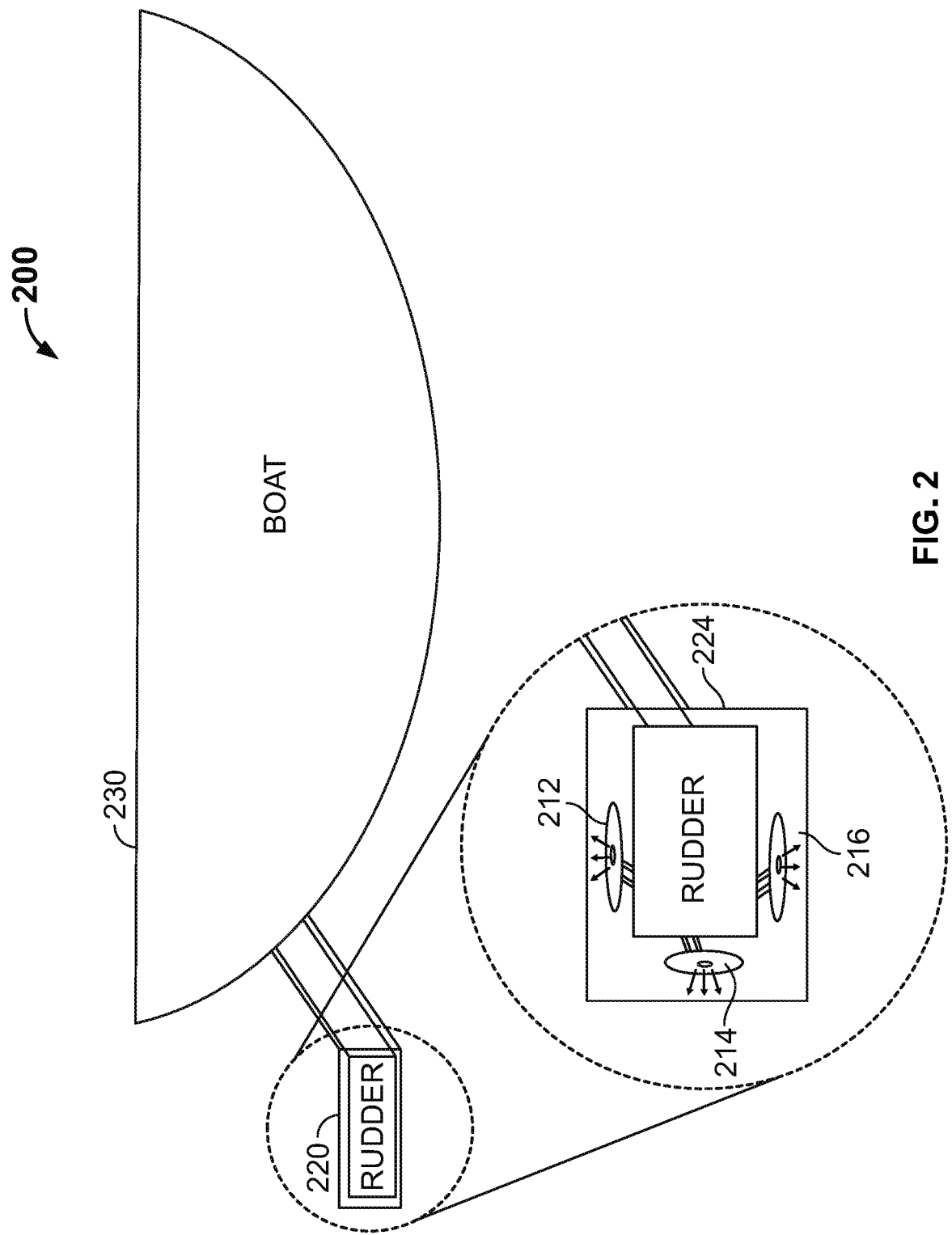
FIG. 2 illustrates another system for internal ultraviolet-C light emitting diode (LED) antifouling in accordance with aspects of the present disclosure.

Referring now to FIG. 2, illustrated is another system for internal ultraviolet-C light emitting diode (LED) antifouling in accordance with aspects of the present disclosure. Using this implementation, biofouling may be prevented on a rudder. In the present implementation, the ultraviolet-C LEDs 212, 214, 216 are installed on the object 220, which is a rudder in the present implementation. The ultraviolet-C LEDs 212, 214, 216 may be disposed within a waterproof, light transmissible potted enclosure 224 around the object 220 (or rudder) underneath a boat 230. The number of ultraviolet-C LEDs in the present implementation are three. This amount is lower than the six LEDs shown in FIG. 1, particularly since the more shallow underwater environment for the internal ultraviolet-C LED antifouling system 200 is, the fewer lights that may be needed since the water is less murky and more easily penetrable at lesser depths.

As stated hereinabove, the number of ultraviolet-C LEDs that are needed to clean the waterproof, light transmissible potted enclosure 224 is location dependent. For example, warmer climates, where more biofouling occurs, may require a greater number of ultraviolet-C LEDs. A person of ordinary skill in the art would be able to determine the number of ultraviolet-C LEDs needed for a particular application.

Figure 3:
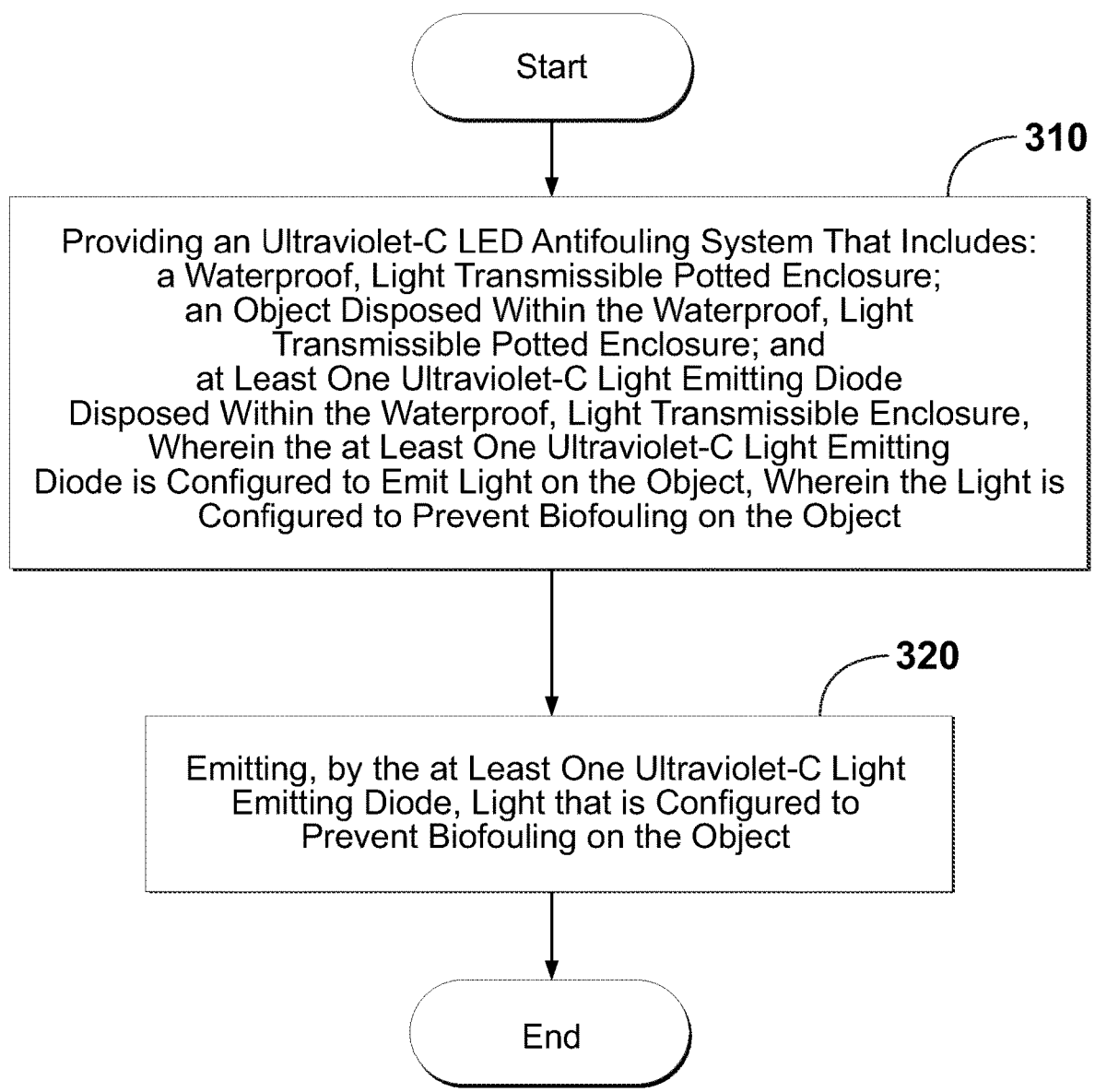
FIG. 3 illustrates a flow chart for a method for internal ultraviolet-C light emitting diode (LED) antifouling in accordance with aspects of the present disclosure.

Referring now to FIG. 3, illustrated is a flow chart for a method for low-power cleaning of undersea objects in accordance with aspects of the present disclosure. At step 310, the method includes providing an ultraviolet-C LED antifouling system that includes: a waterproof, light transmissible potted enclosure; an object disposed within the waterproof, light transmissible potted enclosure; and at least one ultraviolet-C light emitting diode disposed within the waterproof, light transmissible enclosure. The at least one ultraviolet-C light emitting diode is configured to emit light on the object, wherein the light is configured to prevent biofouling on the object.

At step 320, the method includes emitting, by the at least one ultraviolet-C light emitting diode, light that is configured to prevent biofouling on the object. The step of emitting light configured to prevent biofouling may include the step of causing one or more ultraviolet-C light emitting diodes to flash at a rate and time that removes biofouling from the underwater object. For example, the duty cycle of the flashing LEDs may be 50% on and 50% off.

The foregoing description of various embodiments have been presented for purposes of illustration and description. It is not intended to be exhaustive or to limit the system and method to the precise forms disclosed, and obviously many modifications and variations are possible in light of the above teaching. The example embodiments, as described above, were chosen and described in order to best explain the principles of the system and method and their practical application to thereby enable others skilled in the art to best utilize them in various embodiments and with various modifications as are suited to the particular use contemplated. It is intended that the scope of the invention be defined by the claims appended hereto.

What is claimed as new and desired to be protected by Letters Patent of the United States is:

1. An antifouling system, comprising:
   a waterproof, light transmissible enclosure;
   an object disposed within the waterproof, light transmissible enclosure;
   at least one ultraviolet-C light emitting diode disposed within the waterproof, light transmissible enclosure, wherein the at least one ultraviolet-C light emitting diode is configured to emit light through the waterproof, light transmissible enclosure, wherein the light is configured to prevent biofouling on the waterproof, light transmissible enclosure; and
   a potting compound filling the waterproof, light transmissible enclosure around the object and the at least one ultraviolet-C light emitting diode.

2. The antifouling system of claim 1, further comprising:
   a positioner configured to position the antifouling system underwater.

3. The antifouling system of claim 1, wherein the object is underwater.

4. The antifouling system of claim 1, wherein the waterproof, light transmissible enclosure is composed, at least in part, of fused quartz.

5. An antifouling system, comprising:
a waterproof, light transmissible enclosure;
an object disposed within the waterproof, light transmissible enclosure; and
at least one ultraviolet-C light emitting diode disposed within the waterproof, light transmissible enclosure, wherein the at least one ultraviolet-C light emitting diode is configured to emit light through the waterproof, light transmissible enclosure, wherein the light is configured to prevent biofouling on the waterproof, light transmissible enclosure,
wherein the waterproof, light transmissible enclosure is disposed within at least one array node.

6. The antifouling system of claim 5, further comprising:
a positioner configured to position the antifouling system underwater,
wherein the positioner includes a float and an anchor.

7. The antifouling system of claim 5, wherein the object is a sensor.

8. The antifouling system of claim 5, wherein the at least one ultraviolet-C light emitting diode is configured to blink at a flashing rate that still prevents the biofouling.

9. The antifouling system of claim 5, further comprising:
a positioner configured to position the antifouling system underwater,
wherein the positioner includes an anchor, which is a bottle containing a battery, acoustics processing electronics, and storage media for the object.

10. An antifouling method for the antifouling system of claim 5, comprising:
providing the antifouling system that includes:
the waterproof, light transmissible enclosure;
the object disposed within the waterproof, light transmissible enclosure;
the at least one ultraviolet-C light emitting diode disposed within the waterproof, light transmissible enclosure, wherein the at least one ultraviolet-C light emitting diode is configured to emit the light through the waterproof, light transmissible enclosure, wherein the light is configured to prevent biofouling on the waterproof, light transmissible enclosure; and
wherein the waterproof, light transmissible enclosure is disposed within at least one array node; and
emitting, by the at least one ultraviolet-C light emitting diode, the light that is configured to prevent biofouling on the waterproof, light transmissible enclosure.

11. The antifouling method of claim 10, wherein the object is a sensor.

12. An antifouling system, comprising:
a waterproof, light transmissible potted enclosure;
an object disposed within the waterproof, light transmissible potted enclosure;
at least one ultraviolet-C light emitting diode disposed within the waterproof, light transmissible potted enclosure, wherein the at least one ultraviolet-C light emitting diode is configured to emit ultraviolet-C light through the waterproof, light transmissible potted enclosure, wherein the ultraviolet-C light is configured to prevent biofouling on the waterproof, light transmissible potted enclosure; and
a positioner configured to position the antifouling system underwater, wherein the positioner includes an anchor and a float, and wherein the antifouling system is disposed underwater.

13. The antifouling system of claim 12, further comprising:
an array cable having at least one array node,
wherein the waterproof, light transmissible potted enclosure is disposed within the at least one array node.

14. The antifouling system of claim 12, wherein the object is a sensor.

15. The antifouling system of claim 12, wherein the waterproof, light transmissible potted enclosure is composed, at least in part, of fused quartz.

16. The antifouling system of claim 12, wherein the object is a rudder underneath a boat.

17. The antifouling system of claim 12, wherein the at least one ultraviolet-C light emitting diode is configured to blink at a flashing rate that still prevents the biofouling.

18. The antifouling system of claim 12, further comprising:
a positioner configured to position the antifouling system underwater,
wherein the positioner includes an anchor, which is a bottle containing a battery, acoustics processing electronics, and storage media for the object.

* * * * *